United States Patent [19]

Albright

[11] Patent Number: 4,971,764
[45] Date of Patent: Nov. 20, 1990

[54] METHOD AND APPARATUS FOR VENTING STERILIZERS HAVING A LIQUID LOAD

[75] Inventor: Donald W. Albright, Rochester, N.Y.

[73] Assignee: MDT Corporation, Torrance, Calif.

[21] Appl. No.: 19,344

[22] Filed: Feb. 26, 1987

[51] Int. Cl.⁵ .............................................. A61L 2/06
[52] U.S. Cl. .................................... 422/110; 422/113;
422/115; 422/26; 422/103; 436/55; 436/147;
436/148
[58] Field of Search ................ 422/110, 112, 26, 103,
422/113, 115; 436/55, 147, 148

[56] References Cited

U.S. PATENT DOCUMENTS 3,107,975 10/1963 Linder .................................. 422/115
4,003,703 1/1977 Montgomery, Jr. et al. .... 422/26 X
4,164,538 8/1979 Young et al. .................... 422/110 X
4,203,947 5/1980 Young et al. ...................... 422/26 X
4,261,950 4/1981 Bainbridge et al. ................... 422/26
4,263,258 4/1981 Kalasek .............................. 422/26 X
4,309,381 1/1982 Chamberlain et al. ........... 422/26 X Primary Examiner—Robert J. Warden
Assistant Examiner—Lynn M. Kummert
Attorney, Agent, or Firm—Trask, Britt & Rossa

[57] ABSTRACT

The venting mechanism for discharging steam from a sterilizing chamber has a variable effective orifice area controllable in response to decreasing pressure. The throughput of the venting mechanism increases as the pressure decreases, thereby compressing the venting stage of a sterilization cycle without increasing the loss of liquid inherently experienced in sterilizing liquid loads.

14 Claims, 3 Drawing Sheets

METHOD AND APPARATUS FOR VENTING STERILIZERS HAVING A LIQUID LOAD

The present invention is directed to an improved method and apparatus for venting sterilizers having liquid loads.

Steam sterilizers are used to disinfect or sterilize a variety of items such as surgical instruments, towels and liquids, including media used for culturing cells. The sterilizing of liquid loads at pressures above atmospheric pressure presents certain problems in venting the chamber back to its lower pressure and temperature. Care must be taken to avoid any unnecessary loss of the liquid being sterilized. AAMI (Association For the Advancement of Medical Instruments) and various other agencies such as the Federal Procurement Specifications, VA (Veterans Administration) and CSA (Canadian Standards Association) set forth certain standards for liquid loss during venting. Generally a loss of more than approximately 5% is unacceptable. In order to avoid unacceptable losses, the venting of a sterilizer having a liquid load is currently accomplished through a slow bleed valve which lowers the temperature and pressure of the chamber at a very slow rate. Typically these bleed valves have an opening in the order of 0.0625" (0.1587 cm).

Applicant has invented an improved apparatus and method for venting of sterilizers having a liquid load placed therein.

SUMMARY OF THE INVENTION

This invention provides a modified apparatus which compresses the venting stage of a conventional steam sterilizer cycle without substantially increasing the losses experienced from liquid loads. Rather than utilizing a bleed valve sized to limit the venting rate during the initial portion of the venting stage, this invention utilizes a venting mechanism of variable throughput capacity responsive to changing pressure (and/or temperature) conditions within the sterilization chamber. This variable throughput capacity corresponds to a variable flow coefficient of a valve and can be effected by changing the effective area of the passage, orifice or other opening of a valve or equivalent venting mechanism. By "effective area" is meant the actual area through which steam is vented under conditions in which this area is fixed or the weighted average area through with steam is vented under conditions in which this area varies during segments of elapsed time.

The throughput capacity of the venting mechanism may be controlled by various mechanical expedients, including the intermittent opening and closing of a bleed valve. A valve of very large flow coefficient may be used, being operated at a duty cycle which provides an effective area during the initial portion of the venting stage which appoximates that of the bleed valve conventionally used for venting steam from sterilizers. The duty cycle is then modified in response to decreasing pressure and/or temperature conditions within the chamber to provide a substantially increased effective area. For example, the effective flow coefficient of the venting mechanism may typically increase from about 0.8 at the commencement of venting to approximately 5 near completion of venting to atmospheric pressure.

The effective flow coefficient of the venting mechanism is controlled by sensing and circuit means operative to maintain a venting rate which avoids unacceptable liquid losses. Both the temperature and pressure within the sterilization chamber decrease during the venting procedure, but pressure is generally the preferred parameter to monitor in the practice of this invention. The rate at which pressure decreases within the chamber provides a convenient control reference from which to adjust the effective flow coefficient of the venting mechanism. Ideally, the effective flow coefficient, and thus the throughput of the venting mechanism, is controlled to maintain an approximately constant rate of pressure decrease within the chamber. In practice, a rate of below about 1½ pounds per minute pressure reduction should be maintained, with rates below about 1 pound per minute being presently preferred.

DETAILED DESCRIPTION OF THE INVENTION

Figure 1:
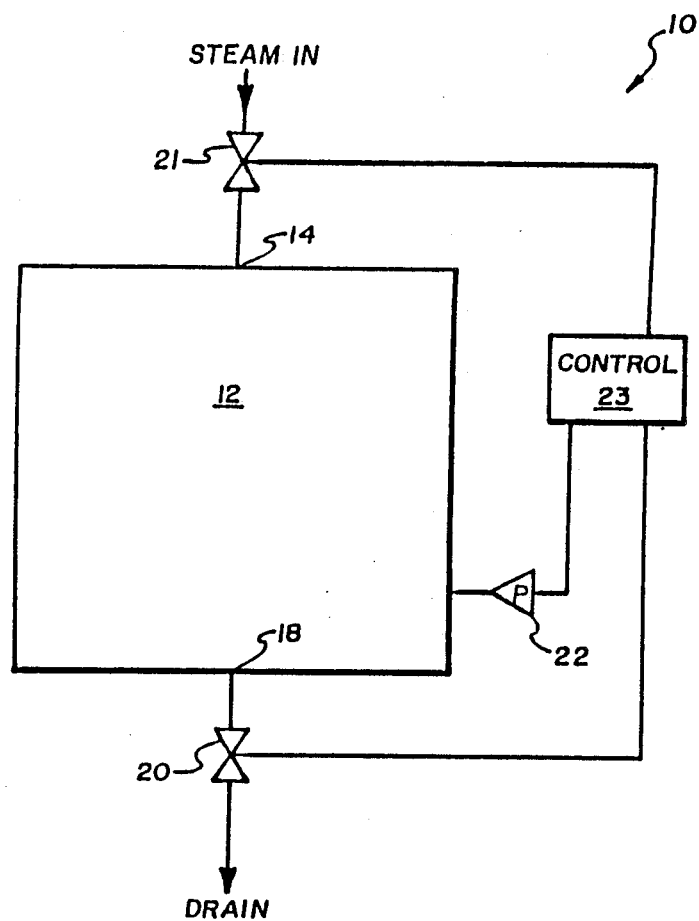
FIG. 1 is a schematic diagram of a sterilizer made in accordance with the present invention.

Referring to FIG. 1 there is illustrated a schematic diagram of a sterilizer which is permanently installed at a facility having access to a steam line and drain. The sterilizer 10 has a sterilization chamber 12 which is connected to a source of steam available at the installation through inlet 14. The chamber has outlet 18 for draining of excess liquid and steam therefrom. The outlet 18 of chamber 12 is connected to the inlet of valve 20. The valve 20 has an outlet which is connected to drain. In the particular embodiment illustrated, valve 20 is a solenoid valve having an opening in the order of about ¾" (1.905 cm). Valve 20 provides means for adjusting the flow rate of the steam exiting chamber 12. It is to be understood that FIG. 1 is a schematic diagram of the invention illustrating those elements necessary for the practice of the present invention and that various other elements normally used with sterilizers may be provided as is commonly done with sterilizers of this type. Monitor means 22 is provided for monitoring the condition of the chamber 12. In the particular embodiment illustrated the monitor 22 is a pressure transducer for monitoring the pressure within chamber 12. Sterilizer 10 is further provided the control means 23 for interpreting the information provided by monitor device 22 and for appropriately controlling the flow of steam into and out of the chamber 12 by opening and closing the appropriate valves. The particular control means may be any control means such as is presently used in sterilizing.

In the operation of sterilizer 10, the chamber 12 is first filled with a liquid load to be sterilized. Typically, a liquid load comprises a plurality of vessels, containing a liquid, for example culture media. After the chamber 12 has been loaded, the door (not shown) of the chamber 12 is closed, thereby providing a substantially air tight chamber 12 for the introduction of steam at the desired temperature through inlet 14. Typically steam is provided at 121° Centigrade. Since this temperature is above the boiling temperature of water the steam will necessarily be pressurized above atmospheric. A steam temperature of approximately 121° Centigrade requires pressurization to approximately 15 pounds per square inch about atmosphere pressure. The chamber is kept at the desired temperature for the preselected time period required for the liquid load placed therein. After the sterilization cycle is completed, the chamber 12 is brought back to its stable temperature at atmosphere pressure through a venting procedure. During this venting procedure great care must be taken to prevent eruption of the liquid load. If the pressure is brought down too quickly it will cause the liquid load to boil or erupt, resulting in unacceptable liquid losses.

The pressure transducer 22 relays the appropriate reading to control means 23. Valve 20 is open and/or closed in response to the appropriate signals sent by the control 23. The valve 20 is intermittently opened and closed. The pressure in the chamber 12 is thereby reduced at a preselected rate, which while relatively rapid compared to conventional practice is nevertheless sufficiently low to avoid boiling off of the liquid load. Preferably, the pressure is reduced at a substantially constant linear rate, typically approximately 1 pound per minute. At this rate, liquid loss is held below approximately 3% Reducing the pressure within the chamber 12 at a rate of 1½ pounds per minute results in liquid losses greater than 5%. During the initial pressure reduction, the solenoid valve 20 is opened for short periods of time at long intervals between openings whereas as the pressure within chamber 12 approaches atmospheric, the pressure valve 20 is opened for longer periods of time at shorter intervals. Valve 20 has a standard flow coefficient (CV) of about 5.0, considerably larger than the CV rating of a typical bleed valve used in prior art steam sterilizers, e.g., 0.08. It can be seen that as valve 20 is left open for longer periods of time, the average throughput of the venting mechanism (valve 20) is increased, thereby permitting venting of chamber 12 average in a shorter time interval than would otherwise be possible. The bleed valves used in prior art steam sterilizers have fixed throughput capacities. The capacities of such valves are determined by the physical characteristics of their openings or orifices.

Figure 3:
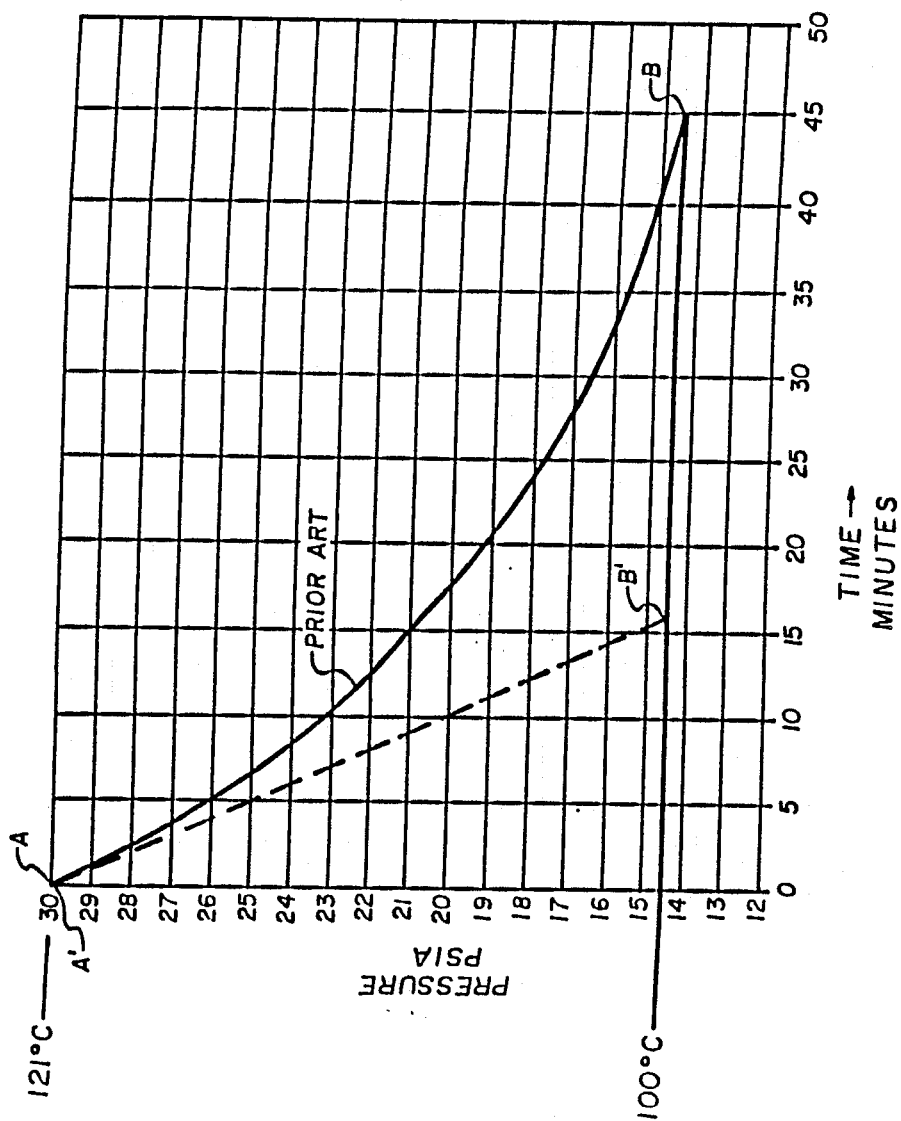
FIG. 3 is a graphical comparison of the rate of reduction of pressure/temperature during the respective venting cycles of a prior art device and a device made in accordance with the present invention.

Referring to FIG. 3, there is illustrated in graphical form two curves which compare the pressure and temperature histories within the respective sterilizing chambers of an apparatus of the prior art and an apparatus made in accordance with the present invention during corresponding venting procedures in which the pressure and temperature conditions within the chamber were reduced by means of controlled venting of steam from 121° C. at approximately 30 psia to approximately 100° C. at atmospheric pressure. The solid line represents the venting cycle of an apparatus according to the prior art. Starting at point A and terminating at point B, this curve represents the drop in pressure of steam from a temperature of 121° (point A) until it reaches approximately 100° Centigrade at atmospheric pressure (point B). The venting mechanism of the prior art sterilizer was a slow bleed passage typical in the prior art. It can be seen that the venting time necessary to reduce the pressure to atmospheric was approximately 47 minutes.

The dash line of FIG. 3 represents the venting procedure of an apparatus made in accordance with the present invention. Reduction of the pressure within the chamber to atmospheric pressure in accordance with the present invention occurred in a substantially linear manner and within a period of approximately 17 minutes. The liquid loss within the chamber was kept to approximately 3% while significantly compressing the venting procedure, and as a consequence the time required to complete a sterilization cycle.

The curves plotted on FIG. 3 demonstrate the advantages of the venting procedure made possible by the present invention. Increasing the throughout capacity of the venting mechanism in response to decreasing pressure within the chamber maintains a relatively constant rate of pressure reduction. This constant rate is reflected by the nearly linear plot A'-B' and is in stark contrast to the continuously decreasing rate of pressure reduction reflected by the plot A-B. As illustrated, the initial slope of the curve A'-B' is not appreciably greater than the initial scope of curve A-B, indicating that the tendency of liquid to erupt or boil off during the initial portion of the venting procedure of this invention is approximately equivalent to that experienced under conventional venting procedures. In any event, the slope of the curve A'-B' characteristic of an apparatus of this invention may be established as desired to effect venting within a relatively short time period but at a rate which holds boil-off losses to within acceptable limits. A temperature and/or pressure monitoring device, such as the pressure transducer 22 illustrated, in effect monitors the slope of the curve A'-B', and associated control means 23 maintains that slope by approximately increasing the effective flow coefficient (CV)—and thus the throughput—of the venting mechanism 20. Of course, the slope of the curve A'B' need not be linear as shown. It may be increased or decreased as desired to take into account the anticipated boil-off losses under the reducing temperature and pressure conditions actually existing in the chamber at any elapsed time interval during the venting procedure. In practice, an increased rate of pressure reduction may be tolerable in the final portion of the venting procedure. In other instances, it may be desirable to establish a relatively low rate of pressure reduction at the beginning of the venting procedure, and to increase the rate during subsequent periods. The control means 23 may be programmed to adjust the throughput capacity of the venting mechanism according to the pressure reduction schedule desired under a variety of specific circumstances.

Figure 2:
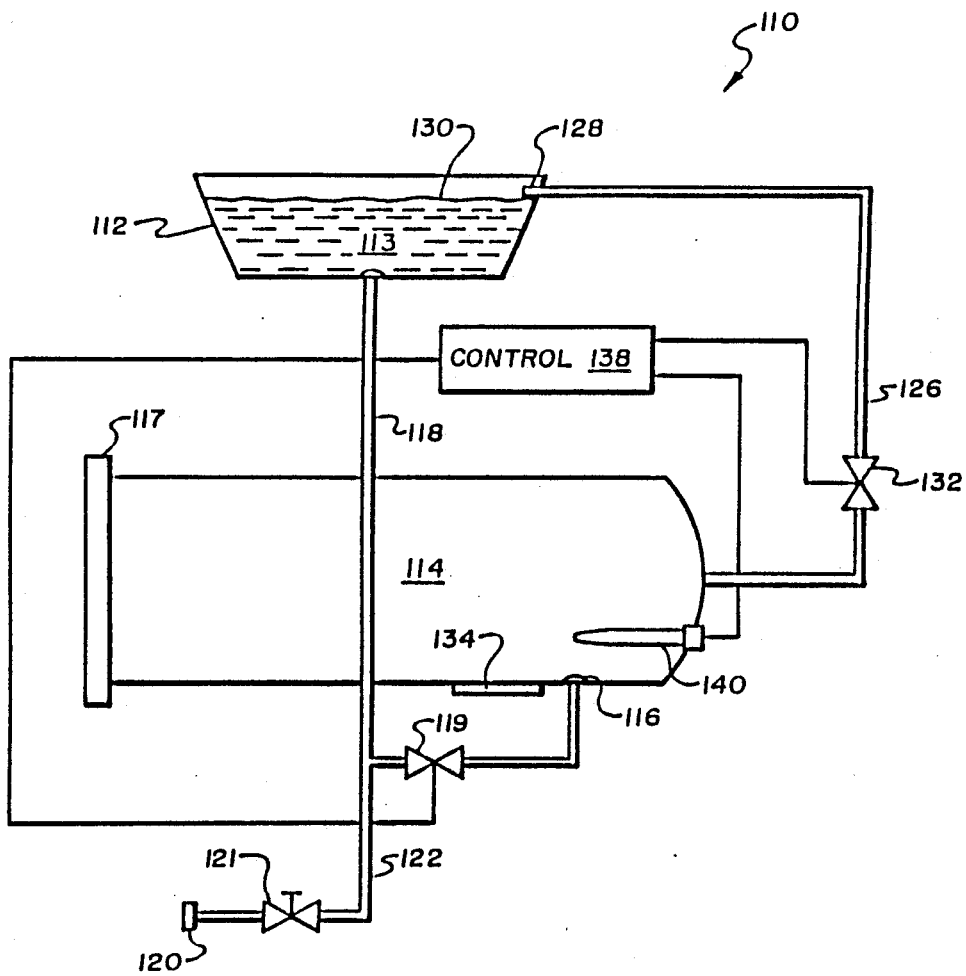
FIG. 2 is a schematic diagram of an unplumbed sterilizer made in accordance with the present invention.

Referring to FIG. 2 there is illustrated a sterilizer 110 also made in accordance with the present invention. The sterilizer 110 is unplumbed meaning that it is not hooked up to any external plumbing for the introduction of steam. Any steam required by sterilizer 110 will be provided by the unit itself. Accordingly, the sterilizer is provided with a reservoir 112 for holding a quantity of water 113. The sterilization chamber 114 has an inlet/outlet port 116 which is connected to the reservoir 112 by passageway 118 which acts as a conduit for the passage of water from reservoir 112 into chamber 114. Valve 119 is provided for opening and closing passageway 118. The port 116 is connected to drain plug 120 by passageway 122 through manual valve 121 for draining the reservoir or chamber of water. In the particular embodiment illustrated a drain plug 120 is provided thereby making manual valve 121 optional. A second passageway 126 between the reservoir 112 and sterilization chamber 114 is provided to allow venting of steam/air from chamber 112 directed to the atmosphere. Accordingly, the outlet 128 of passageway 126 is placed above the water line 130. A valve 132 is passageway 126 is provided to maintain the passageway open or closed.

In the particular embodiment illustrated valves 132 and 119 are solenoid valves and are appropriately opened or closed by control unit 138. A heating member 134 is attached to chamber 114 for turning the water into steam and heating the steam to the desired temperature. Heating element 134 is controlled by a control box 138. A temperature sensor 140 is provided within chamber 114 for monitoring the temperature of the steam therein.

Initially the reservoir 112 is filled with an appropriate amount of water. The sterilizing chamber 114 is loaded with an appropriate liquid load. The chamber is sealed by a door 117. A predetermined amount of water is allowed to flow from reservoir 112 through passageway 118, valve 119 and port 116 into sterilization chamber 114. Heating element 134 is activated to change the water into steam and heated to the selected temperature. The steam is maintained at the desired temperature, for example 121° C., for the preselected period of time. After the sterilization portion of the cycle has been completed, the sterilizer 110 goes into the venting mode to lower the temperature and pressure in chamber 114 so the door 117 may be opened. For this purpose the temperature sensing means 140 monitors the condition of the steam chamber 114 and relays this information to control unit 138. The control unit 138 by appropriate electrical means (not shown) opens valve 119 allowing steam to re-enter the reservoir at the bottom of the reservoir and bubble or condense through the water present therein. The returning of the steam through the water in the reservoir provides several advantages. This recycle helps to reclaim the water initially placed in the reservoir. If steam is allowed to be vented directly out of the sterilizer it tends to splatter and create noise during the venting phase. The valve 119 is opened and closed periodically, in the same manner discussed with respect to valve 20 of FIG. 1, such that the temperature within the chamber 114 is reduced in a substantially linear fashion. In the particular embodiment illustrated the temperature was reduced at a rate of ½° C. per ½ minute for liquid loss of about 3%. During he initial reduction of temperature the valve 119 is opened for short periods of time at relatively long spaced intervals. As the temperature is lowered the valve 119 stays open for longer periods of time at smaller time intervals. Once the temperature of the steam within the chamber reaches a predetermined temperature, generally in the range of 103° C. to 108° C. and preferably about 105° C., valve 119 is closed and the steam in the chamber is allowed to vent to atmosphere through passage 126 by opening valve 132. Because the temperature at this point is relatively low, valve 132 remains open. However, if venting through valve 132 occurs at a sufficient high temperature, then valve 132 may be opened and closed in the same manner as valve 119. In the particular embodiment illustrated valves 119 and 132 each have a CV value of about 0.5. This is in contrast to a comparable sized device of the prior art which would use a bleed valve having a CV value of about 0.02. The steam may be vented through passageway 118 so long as the steam has sufficient amount of head pressure to prevent the water from flowing back into the chamber 114.

When the steam temperature is reduced to about 100° Centigrade, the door 117 to chamber 114 may be opened.

Various modifications may be made without departing from the scope of the present invention. For example, any desired type valve or heating means may be used. The sterilization chamber may be provided with a jacket.

What is claimed is:

1. A method of venting a sterilizer having a liquid load therein, said sterilizer having a sterilizing chamber, sensing means for monitoring the pressure within said sterilizing chamber and a venting mechanism with a variable throughput capacity responsive to said sensing means comprising the step of:
    venting steam from said sterilizing chamber after a sterilizing cycle through sad venting mechanism while adjusting the throughput capacity of said venting mechanism in response to drops in pressure within said chamber to effect a rate of venting said stem from said chamber which does not substantially decrease with time;

2. A method of venting an unplumbed sterilizer having a liquid load therein, said sterilizer having a sterilizing chamber, a reservoir filled with water, temperature or pressure sensing means disposed within said sterilizing chamber, and a venting mechanism with a variable throughput capacity operably associated with said chamber, comprising the step of:
    venting stem from said sterilizing chamber through said venting mechanism after a sterilizing cycle through said water in said reservoir at a rate which increases in response to decrease in the pressure or temperature in said chamber.

3. A method according to claim 2 wherein said venting of said sterilizing chamber through said reservoir is at a rate which effects a substantially linear decrease in temperature within said chamber.

4. A method according to claim 3 wherein the temperature in said chamber is reduced at a rate of about ½ degree centigrade per ½ minute.

5. A method according to claim 2 wherein venting of said sterilizing chamber through said water in said reservoir is done through a plurality of short timed releases.

6. A method according to claim 2 wherein said venting through said water is continued until a first predetermined temperature is achieved within said chamber and venting of steam from the chamber is thereafter done directly to the atmosphere.

7. A method of venting an unplumbed sterilizer according to claim 2 wherein the pressure in said chamber is reduced at a rate of about 1 psi per minute.

8. A sterilizing apparatus comprising:
    a sterilizing chamber;
    sensing means disposed within said chamber or monitoring the pressure within said chamber;
    valve means mechanically associated with said chamber, operable to vent steam from said chamber;
    control means operably associated with said valve means and said sensing means for opening and closing said valve means intermittently at a rate to vent steam from said chamber to effect a pressure drop within said chamber at a substantially linear rate below about 1½ pounds per minute.

9. A sterilizing apparatus comprising:
    a sterilizing chamber;
    sensing means disposed within said chamber for monitoring either or both the temperature and pressure within said chamber;
    valve means selectively operable to vent steam from said chamber to the atmosphere;
    control means connected in circuit between said valve means and said sensing means, to operate said valve means in response to said sensing means such that the rate of pressure drop within said chamber does not substantially decrease during venting.

10. In a sterilizer operated to effect elevated temperature and pressure conditions within a closed chamber during a procedure for sterilizing liquid loads, including a venting mechanism operable to vent steam from said chamber during a venting period, thereby to reduce the pressure within said chamber to approximately atmospheric pressure, the improvement which comprises:

a venting mechanism operable to effect a variable flow coefficient;

sensing means positioned to monitor either or both the temperature and pressure within said chamber; and control means operably associated with said venting mechanism and responsively associated with said sensing means to provide an increased effective flow coefficient for said venting mechanism corresponding to decreases in pressure within said chamber during said venting period.

11. An improvement according to claim 10 wherein said control means is adapted to operate said venting mechanism to control the rate of pressure drop within said chamber to maintain losses of liquid from said liquid load to below about five percent (5%) during said venting period.

12. An improvement according to claim 11 wherein said control means is adapted to maintain the rate of pressure drop within said chamber below about 1½ pounds per minute.

13. An improvement according to claim 12 wherein said control means is adapted to maintain the rate of pressure drop within said chamber within the range of about 1 to about 1½ pounds per minute.

14. An improvement according to claim 10 wherein said control means is adapted to operate said venting means to control the rate of temperature drop within said chamber at less than about 1° C. per minute.

* * * * *